(12) United States Patent
Schnaufer et al.

(10) Patent No.: US 10,336,383 B2
(45) Date of Patent: Jul. 2, 2019

(54) COMPONENT FOR A VEHICLE

(71) Applicant: Bayerische Motoren Werke Aktiengesellschaft, Munich (DE)

(72) Inventors: Thomas Schnaufer, Oberhausen (DE); Jan Jaap Timmerman, Munich (DE); Peter Jahnke, Neufahrn (DE); Andre Koch, Munich (DE)

(73) Assignee: Bayerische Motoren Werke Aktiengesellschaft, Munich (DE)

( * ) Notice: Subject to any disclaimer, the term of this patent is extended or adjusted under 35 U.S.C. 154(b) by 324 days.

(21) Appl. No.: 15/201,674

(22) Filed: Jul. 5, 2016

(65) Prior Publication Data

US 2016/0311482 A1    Oct. 27, 2016

Related U.S. Application Data

(63) Continuation of application No. PCT/EP2014/077101, filed on Dec. 10, 2014.

(30) Foreign Application Priority Data

Jan. 9, 2014   (DE) .................. 10 2014 200 248

(51) Int. Cl.
*B62D 65/00* (2006.01)
*B62D 29/04* (2006.01)
*G01M 17/00* (2006.01)
*G01N 1/04* (2006.01)
*B29L 31/30* (2006.01)

(52) U.S. Cl.
CPC ......... *B62D 65/005* (2013.01); *B62D 29/043* (2013.01); *G01M 17/00* (2013.01); *G01N 1/04* (2013.01); *B29L 2031/3005* (2013.01)

(58) Field of Classification Search
CPC ... B62D 65/005; B62D 29/043; G01M 17/00; G01N 1/04; B29L 2031/3005
See application file for complete search history.

(56) References Cited

U.S. PATENT DOCUMENTS

2014/0079908 A1*  3/2014  Kato .................. B32B 3/06
                                           428/140

FOREIGN PATENT DOCUMENTS

| CN | 1766587 A    | 5/2006  |
| CN | 102297755 A  | 12/2011 |
| CN | 102589421 A  | 7/2012  |
| CN | 102628766 A  | 8/2012  |
| DE | 199 45 556 A1 | 3/2001 |
| DE | 199 45 558 A1 | 3/2001 |
| DE | 102 11 138 A1 | 9/2003 |

(Continued)

OTHER PUBLICATIONS

International Search Report (PCT/ISA/210) issued in PCT Application No. PCT/EP2014/077101 dated Mar. 26, 2015 with English translation (five pages).

(Continued)

*Primary Examiner* — Lori L Lyjak
(74) *Attorney, Agent, or Firm* — Crowell & Moring LLP

(57) ABSTRACT

A component, in particular a body component, for a vehicle, has at least one test section which is arranged in a predetermined area of the component and which is connected in one piece to the rest of the component by way of at least one connecting element. The connecting element is embodied as predetermined breaking point.

6 Claims, 5 Drawing Sheets

(56) References Cited

FOREIGN PATENT DOCUMENTS

DE     20 2007 003 905 U1     7/2008
EP     2 671 779 A1     12/2013

OTHER PUBLICATIONS

German-language Written Opinion (PCT/ISA/237) issued in PCT Application No. PCT/EP2014/077101 dated Mar. 26, 2015 (five pages).
German Search Report issued in counterpart German Application No. 10 2014 200 248.6 dated Sep. 29, 2014 with partial English translation (13 pages).
Chinese Office Action issued in counterpart Chinese Application No. 201480056109.5 dated Dec. 30, 2016 with English translation (13 pages).

\* cited by examiner

COMPONENT FOR A VEHICLE

CROSS REFERENCE TO RELATED APPLICATIONS

This application is a continuation of PCT International Application No. PCT/EP2014/077101, filed Dec. 10, 2014, which claims priority under 35 U.S.C. § 119 from German Patent Application No. 10 2014 200 248.6, filed Jan. 9, 2014, the entire disclosures of which are herein expressly incorporated by reference.

BACKGROUND AND SUMMARY OF THE INVENTION

The invention relates to a component, in particular a body component, for a vehicle.

Furthermore, the invention relates to a method for producing a component, in particular a body component, for a vehicle.

For quality assurance in the production of body components for vehicles, the body components which are produced have to be subjected to a test of their respective properties or tested whether said properties meet predetermined requirements.

In the production of a body component from fiber composite material, the material used for this purpose is produced during the production of the component. Testing of material properties can therefore take place only indirectly via tests undertaken before the production of the component. A direct test of properties of the material when the component is completed is possible to date only in a relatively complicated manner over the course of testing individual components. However, such individual tests are not statistically evaluable on an industrial scale, that is to say, in the mass production of components, and are therefore only inadequately available for quality assurance.

It is the object of the invention to provide for quality testing of components produced in large piece numbers, in particular body components, for vehicles.

This and other objects are achieved by a component, as well as a method for producing same, in particular a body component for a vehicle, wherein at least one test portion is arranged in a predeterminable region of the component and is connected integrally to the rest of the component via at least one connecting element designed as a predetermined breaking point.

According to the invention, the component of the type mentioned at the beginning has at least one test portion which is arranged in a predeterminable region of the component and is connected integrally to the rest of the component via at least one connecting element designed as a predetermined breaking point.

After the production of a component according to the invention, the test portion can be removed from the rest of the component in a simple manner and supplied for quality testing. Since the test portion is part of the component and is therefore produced from the same material as the rest of the component a conclusion can be drawn as to the quality of the entire component from the test portion quality to be tested.

The component is destroyed by the removal of the test portion and is no longer usable. By means of the removal of the plurality of test portions from the components and the associated availability of the plurality of test portions for quality tests, a plurality of statistically evaluable test results can be generated by way of the quality tests. In particular, by correlating process parameters, and by a standardized removal process and standardized removal points, quality assurance can be achieved on an industrial scale.

In addition, an assignment of individual test results to individual components permits the retracing of the production chain in the event of the occurrence of unacceptable deviations in the quality of individual components, as a result of which a determination of the error source and precise monitoring of a production process are possible.

The connecting element may be designed, for example, as a breaking tab.

According to an advantageous refinement, the test portion and at least that region of the component which surrounds the test portion are formed from a fiber composite material. The advantage of the invention is presented in particular in the quality assurance during the production of components from a fiber composite material. For example, a fiber composite plastic may serve as the fiber composite material. The rest of the component may also be formed entirely from a fiber composite material.

According to a further advantageous refinement, at least one connected circumferential portion of the test portion is separated from the rest of the component by a separating method, in particular by water jet cutting or laser cutting. If only one connected circumferential portion of the test portion is separated from the rest of the component, the test portion is connected to the rest of the component via just one single connecting element designed as a predetermined breaking point. If two or more non-connected circumferential portions of the test portion are separated from the rest of the component, the component is connected to the rest of the component via two or more connecting elements designed as a predetermined breaking point. Water jet cutting has the advantage that, during the cutting, virtually no heat is admitted to the test portion and/or to the rest of the component, which admission of heat could change the quality of the test portion in such a manner that a conclusion can only be inadequately drawn from the quality of the test portion as to the quality of the rest of the component.

In a further advantageous embodiment, at least one positioning portion is formed on the test portion. The positioning portion serves for the suitable positioning of the test portion in a testing device used for testing the test portion. This promotes a structurally simple, rapid and automated testing of components produced in high piece numbers, in particular since a suitable positioning of test portions to be tested relative to a testing device is brought about virtually automatically without an apparatus outlay being required for this purpose. It is also possible for two or more corresponding positioning portions to be arranged on the test portion, depending on requirements and/or the design of the test portion. The positioning portion can also be designed as a lug or recess formed on the circumference of the test portion.

Furthermore, according to the invention, in the case of the method of the type mentioned at the beginning, at least one test portion of the component, which test portion is arranged in a predeterminable region of the component, is separated from the rest of the component leaving at least one connecting element which is designed as a predetermined breaking point and connects the test portion integrally to the rest of the component.

The advantages mentioned above with respect to the component are correspondingly associated with the method.

In an advantageous refinement the test portion and at least that region of the component which surrounds the test portion are formed from a fiber composite material. The advantage of the method according to the invention is shown in particular in the quality assurance during the production of components from a fiber composite material. For example, a fiber composite plastic can be used as the fiber composite material.

According to a further advantageous refinement, at least one connected circumferential portion of the test portion is separated from the rest of the component by a separating method, in particular by water jet cutting or laser cutting. The advantages mentioned above with respect to the corresponding refinement of the component are correspondingly associated with this refinement.

It is furthermore considered advantageous if at least one positioning portion is formed on the test portion, which positioning portion serves for the suitable positioning of the test portion in a testing device used for testing the test portion. The advantages mentioned above with respect to the corresponding refinement of the component are also correspondingly associated with this refinement.

Other objects, advantages and novel features of the present invention will become apparent from the following detailed description of one or more preferred embodiments when considered in conjunction with the accompanying drawings.

DETAILED DESCRIPTION OF THE DRAWINGS

Figure 1:
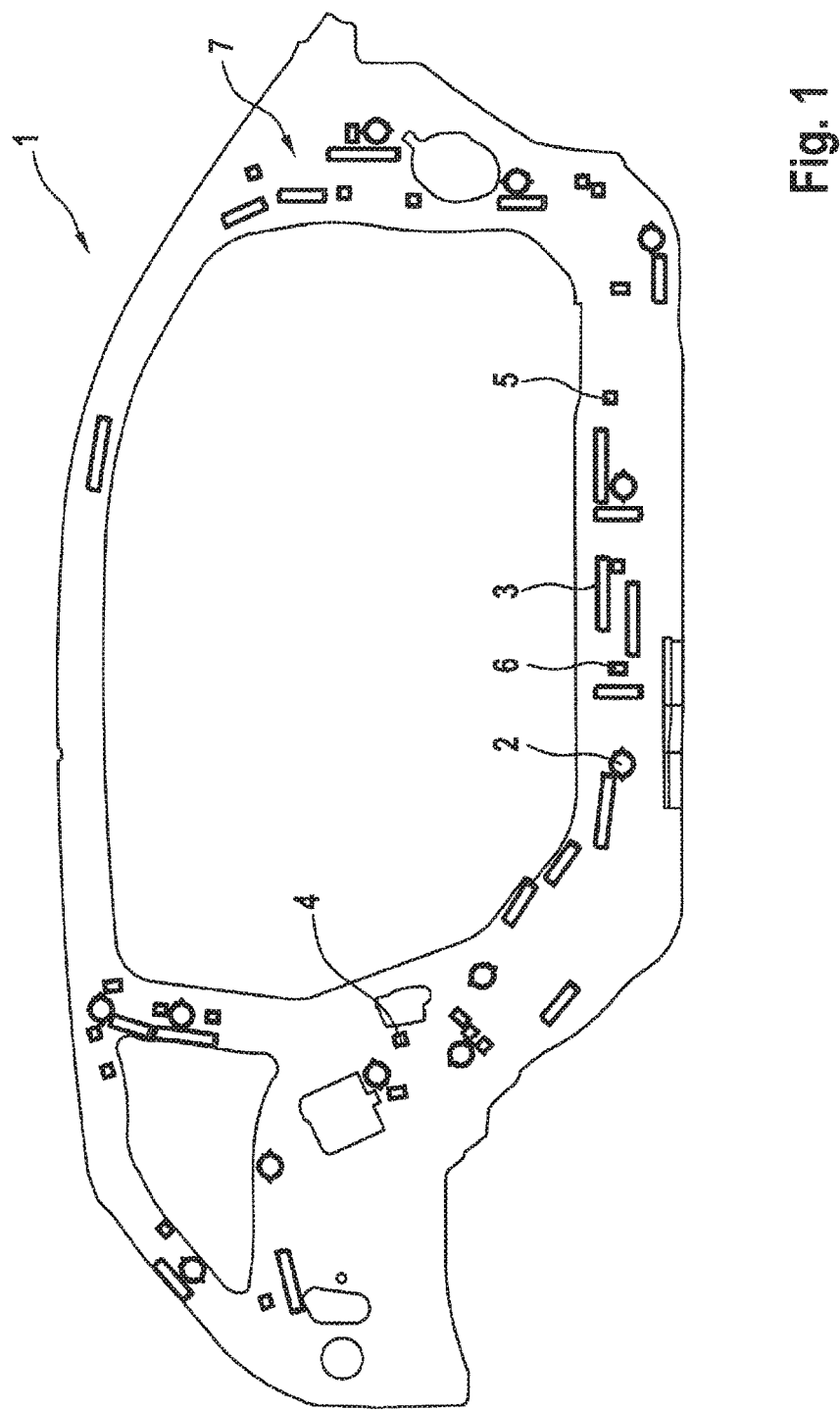
FIG. 1 is a side view of an exemplary embodiment for a component according to the invention.

FIG. 1 shows a side view of an exemplary embodiment of a component 1 according to the invention in the form of a body component, which is formed from a fiber composite plastic, for a motor vehicle (not shown). A test portion 2, 3, 4, 5 or 6 of the component 1 is arranged in each case in predeterminable regions of the component 1. The designs of the test portions 2, 3, 4, 5 and 6 are shown more clearly in FIGS. 2, 3, 4, 5 and 6, respectively.

Figure 2:
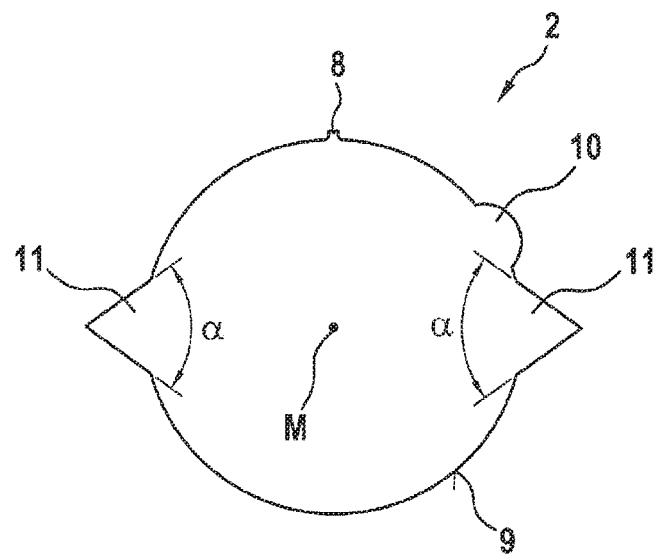
FIG. 2 is a schematic top view of a test portion removed from the component shown in FIG. 1.

FIG. 2 shows a schematic top view of a test portion 2 removed from the component shown in FIG. 1. The test portion 2 is connected integrally to the rest of the component 7 via a connecting element 8 designed as a predetermined breaking point and as a breaking tab. A single connected circumferential portion 9 of the test portion 2 is separated from the rest of the component 7 by water jet cutting. A positioning portion 10, which is designed as a lug arranged on the circumferential portion 9, is formed on the test portion 2. The positioning portion 10 serves for the suitable positioning of the test portion 2 in a testing device (not shown) used for testing the test portion 2. Furthermore, two testing points 11 are arranged on the circumferential portion 9, on mutually diametrically opposite sides of he test portion 2. Each testing point 11 has two limbs, between which the angle $\alpha=72°$ is arranged. By this means, the test portion 2 can be oriented in a desired manner in a testing device. The test portion 2 is intended to be aligned here along a main fiber direction of the fiber composite material. This can take place by means of a draping simulation, an FE-based deformation simulation or an orientation traced back from an actual component. The test portion 2 can be machined by way of grinding preparation in such a manner that the fiber angle of the fibers of the fiber composite plastic can be determined. Alternatively, the fiber angle can be determined by use of microcomputer tomography. For this purpose, the test portion 2 can be reduced in size if the test portion 2 is too large for a testing device used for the microcomputer tomography. The diameter of the test portion 2 can lie within a range of 30 mm to 45 mm. The distance between the points, which face away from each other, of the testing points 11 can lie within a range of 40 mm to 50 mm. The positioning portion 10 can have a diameter within a range of 5 mm to 10 mm. The distance of that part of the positioning portion 10 which is arranged furthest away from the center point M of the test portion 2 can lie within a range of 10 mm to 15 mm.

Figure 3:
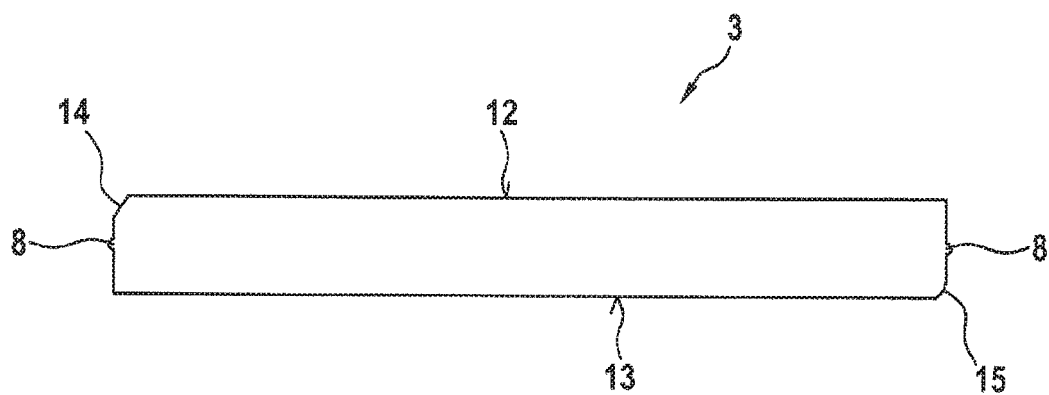
FIG. 3 is a schematic top view of a further test portion removed from the component shown in FIG. 1.

FIG. 3 shows a schematic top view of a further test portion 3 removed from the component shown in FIG. 1. The test portion 3 is connected integrally to the rest of the component 7 via two connecting elements 8 in each case designed as a predetermined breaking point and as a breaking tab. Two connected circumferential portions 12 and 13 of the test portion 2 are separated from the rest of the component 7 by water jet cutting. The test portion 3 can be used for a tension or bending test. In this case, a preform overlapping can also be formed on the test portion 3, i.e. a region in the fiber composite plastic, in which two textile fiber parts mutually overlap, as a result of which the test portion 3 has a greater thickness in this region. An orientation with reference to the geometrical reference of the test portion 3 can be continuously ensured here. A bevel 14 is arranged at the corner, illustrated at the top left, of the test portion 3 and a rounded portion 15 is arranged at the corner, illustrated at the bottom right, of the test portion 3. By means of the bevel 14 and the rounded portion 15, the test portion 3 can be oriented in a testing device. This is relevant in particular if for example, test portions 3 which are subjected to a bending load supply different results when the sample is rotated. By means of a continuous and desired orientation of the test portion 3 in a corresponding testing device, research on the cause of the respective fracture pattern can take place better.

Figure 4:
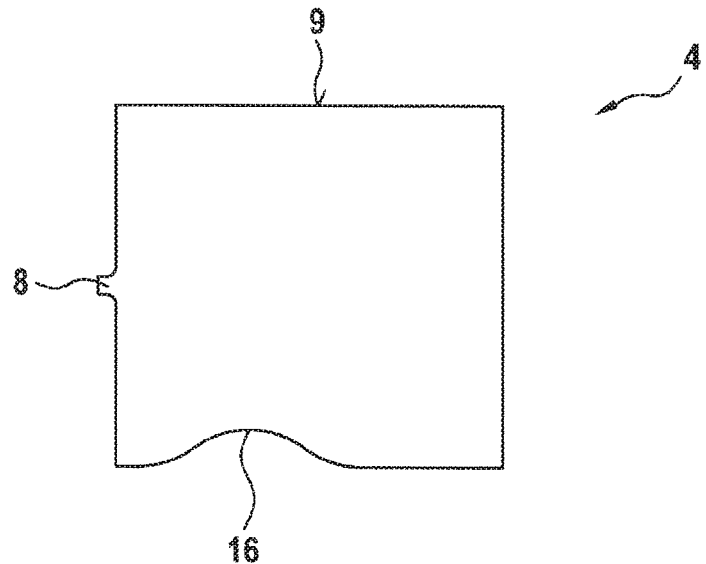
FIG. 4 is a schematic top view of a further test portion removed from the component shown in FIG. 1.

FIG. 4 shows a schematic top view of a further test portion 4 removed from the component shown in FIG. 1. The test portion 4 is connected integrally to the rest of the component 7 via a connecting element 8 designed as a predetermined breaking point and as a breaking tab. A single connected circumferential portion 9 of the test portion 4 is separated from the rest of the component 7 by water jet cutting. The fiber composite plastic of the test portion 4 customarily has a plurality of individual layers which are formed from fibers and have a defined individual layer thickness The individual layer thicknesses can be determined via a grinding sample. A securing portion 16 designed as a recess arranged on the circumferential portion 9 is formed on the test portion 4. The securing portion serves for securing the respective grinding plane used on the grinding sample The geometry of the test portion 4 guarantees unambiguouos assignment of the laminate layers.

Figure 5:
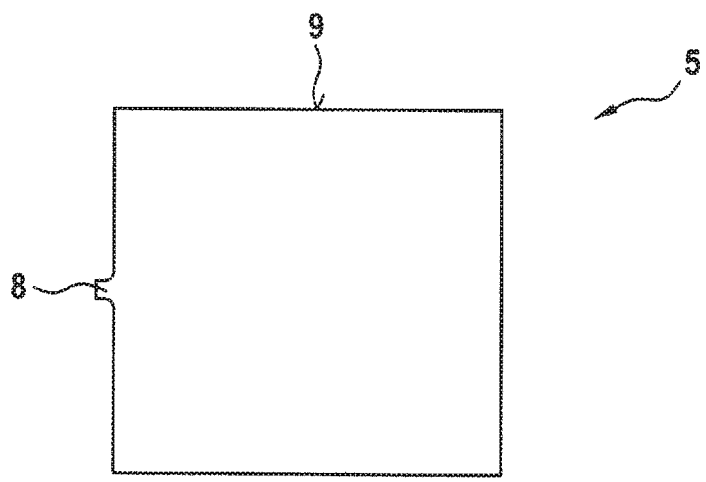
FIG. 5 is a schematic top view of a further test portion removed from the component shown in FIG. 1.

FIG. 5 shows a schematic top view of a further test portion 5 removed from the component shown in FIG. 1. The test portion 5 is connected integrally to the rest of the component 7 via a connecting element 8 designed as a predetermined breaking point and as a breaking tab. A single connected circumferential portion 9 of the test portion 5 is separated from the rest of ti e component 7 by water jet cutting. The test portion 5 can be used for carrying out differential scanning calorimetry (DSC), wherein the respectively dispensed or absorbed quantity of the test portion 5 can be measured during cooling or heating of the test portion 5 or in an isothermic process.

Figure 6:
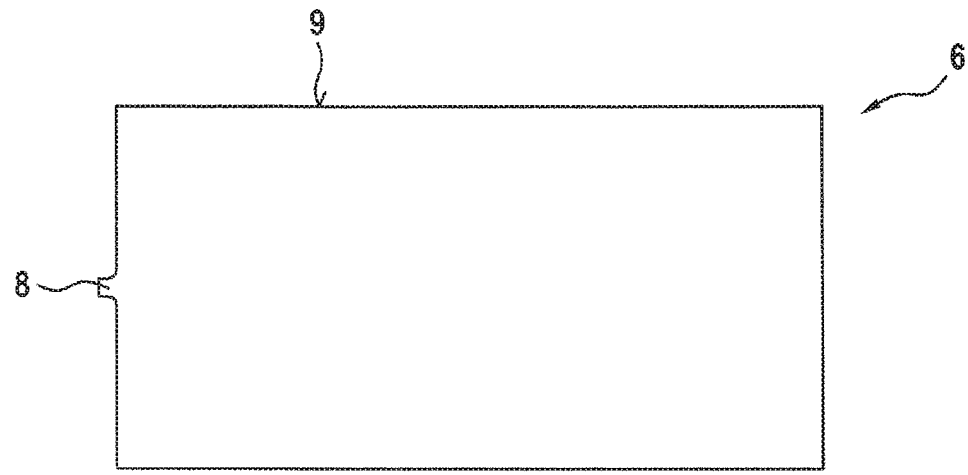
FIG. 6 is a schematic top view of a further test portion removed from the component shown in FIG. 1.

FIG. 6 shows a schematic top view of a further test portion 6 removed from the component shown in FIG. 1. The test portion 6 is connected integrally to the rest of the component 7 via a connecting element 8 designed as a predetermined breaking point and as a breaking tab. A single connected circumferential portion 9 of the test portion 6 is separated from the rest of the component 7 by water jet cutting. The test portion 6 can be used for carrying out thermogravimetric analysis (TGA). The test portion 6 can have a length of 35 mm and a width of 20 mm. The longer sides of the test portion 6 can be oriented at an angle of 90° to the 0° angle of the fiber direction Alternatively, the longer sides of the test portion 6 can be oriented at an angle of 0° to the 0° angle of the fiber direction.

Figure 7:
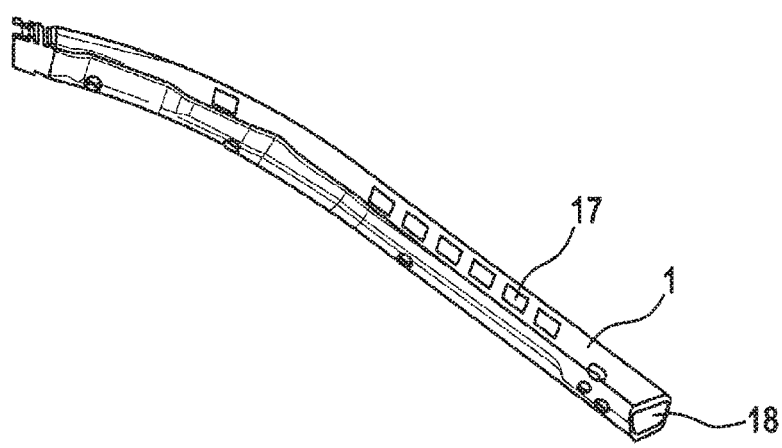
FIG. 7 is a perspective illustration of a detail of an exemplary embodiment for a component according to the invention.

FIG. 7 shows a perspective illustration of a detail of an exemplary embodiment for a component 1 according to the invention in the form of a body component, which is formed from a fiber composite plastic, for a motor vehicle (not shown). The body component subsequently forms an A pillar of a corresponding motor vehicle. The body component is filled with a core material 18, for example a PUR foam, which serves for reinforcing the body component. A test portion 17 of the component 1 is arranged in each case in predeterminable regions of the component 1. The design of the test portions 17 is shown more clearly in FIG. 8.

Figure 8:
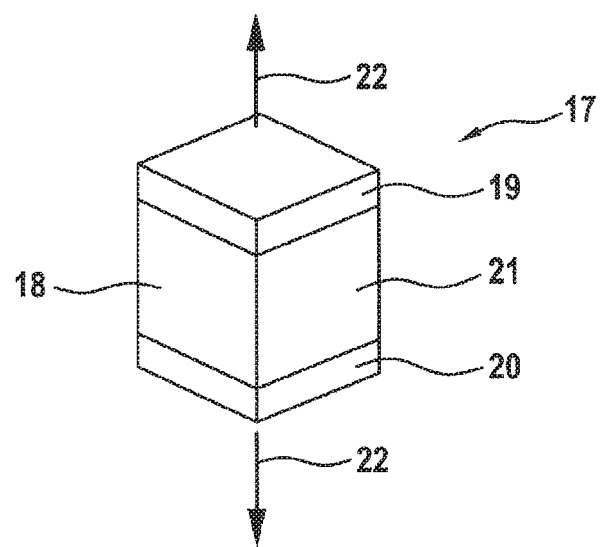
FIG. 8 is a perspective illustration of a test portion removed from the component shown in FIG. 7.

FIG. 8 shows a perspective illustration of a test portion 17 removed from the component shown in FIG. 7. The test portion 17 is of cuboidal design and is connected integrally to the rest of the component 7 via at least one connecting element (not illustrated specifically) designed as a predetermined breaking point and as a breaking tab. At least one connected circumferential portion of the test portion 17 is separated from the rest of the component 7 by water jet cutting. The test portion 17 has two fiber composite layers 19 and 20 and a core material layer 21 arranged in between. In order to test the foam adhesion of a component 1 provided with a PUR core material 18, the test portion 17 can be acted upon with a tensile force orthogonally to the surface of the fiber composite layers 19 and 20 according to the arrows 22 shown in FIG. 8. For this purpose, the test portion 17 can be arranged on a test receptacle which is mounted cardanically on two sides.

LIST OF REFERENCE NUMBERS:

1 Component
2 Test portion
3 Test portion
4 Test portion
5 Test portion
6 Test portion
7 Rest of the component
8 Connecting element
9 Circumferential portion
10 Positioning portion
11 Testing point
12 Circumferential portion
13 Circumferential portion
14 Bevel
15 Rounded portion
16 Securing portion
17 Test portion
18 Core material
19 Fiber composite layer
20 Fiber composite layer
21 Core material layer
22 Arrow
M Center point The foregoing disclosure has been set forth merely to illustrate the invention and is not intended to be limiting. Since modifications of the disclosed embodiments incorporating the spirit and substance of the invention may occur to persons skilled in the art, the invention should be construed to include everything within the scope of the appended claims and equivalents thereof.

What is claimed is:

1. A vehicle component, comprising:
a vehicle body component, wherein
the vehicle body component has at least one test portion arranged in a predetermined region of the vehicle body component,
the at least one test portion is connected integrally to the vehicle body component via at least one connecting element extending in a first direction between the at least one test portion and the vehicle body component, and
the at least one connecting element is configured as a predetermined breaking point having substantially equal dimensions in directions orthogonal to the first direction.

2. The component according to claim 1, wherein
the at least one test portion and at least a region of the vehicle body component surrounding the at least one test portion are made of a fiber composite material.

3. The component according to claim 1, wherein at least one connected circumferential portion of the at least one test portion is separable from a remainder of the vehicle body component.

4. The component according to claim 3, wherein the at least one connected circumferential portion of the at least one test portion is configured to be separable via water jet cutting or laser cutting.

5. The component according to claim 1, further comprising at least one positioning portion formed on the at least one test portion, wherein
the at least one positioning portion serves to suitably position the at least one test portion in a test device used in testing the at least one test portion.

6. The component according to claim 2, further comprising at least one positioning portion formed on the at least one test portion, wherein
the at least one positioning portion serves to suitably position the at least one test portion in a test device used in testing the at least one test portion.

* * * * *